United States Patent [19]

Orentreich

[11] Patent Number: 4,542,129

[45] Date of Patent: Sep. 17, 1985

[54] DHEA FORMULATIONS AND METHODS FOR TREATING DRY SKIN

[76] Inventor: Norman Orentreich, 140 E. 72nd St., New York, N.Y. 10021

[21] Appl. No.: 694,537

[22] Filed: Jan. 24, 1985

Related U.S. Application Data

[63] Continuation-in-part of Ser. No. 408,548, Aug. 16, 1982, abandoned.

[51] Int. Cl.$^4$ .............................................. A61K 31/56
[52] U.S. Cl. ................................................... 514/178
[58] Field of Search .................................. 424/243, 59

[56] References Cited

U.S. PATENT DOCUMENTS 3,162,631 12/1964 Pike ................................ 260/239.57

OTHER PUBLICATIONS

Chemical Abstracts (1969) vol. 70, Par. 34,7768, an abstract of a publication by Pochi et al., "J. Invest. Dermatol.", 1969, 52(1) 32–36.

Chemical Abstracts (1970) vol. 72, par. 118,214n, an abstract of a publication by Oertel et al., "Hoppe-Sayler's Z. Physiol. Chem.", 1970 351(3) pp. 84–86 (Germ.).

*Primary Examiner*—Elbert L. Roberts
*Attorney, Agent, or Firm*—Panitch, Schwarze, Jacobs & Nadel

[57] ABSTRACT

Topical formulations for treating dry skin with dehydroepiandrosterone (DHEA) may contain a keratolytic agent to counteract the formation of acne-like skin lesions without diminishing the effectiveness of DHEA in increasing sebum production. The keratolytic agent may be a hydroxybenzoic acid, alpha-hydroxycarboxylic acid or urea, with salicylic acid being preferred. The DHEA and keratolytic agent may be formulated in a non-toxic, dermatologically acceptable vehicle including tinctures, creams, ointments, gels and lotions.

16 Claims, No Drawings

DHEA FORMULATIONS AND METHODS FOR TREATING DRY SKIN

CROSS REFERENCE TO RELATED APPLICATIONS

This application is a continuation-in-part of my co-pending patent application Ser. No. 408,548 filed Aug. 16, 1982 for "Topical Applications for Preventing Dry Skin", now abandoned which application was in turn related to my U.S. patent application Ser. No. 345,835, filed Feb. 4, 1982, now abandoned.

FIELD OF THE INVENTION

The present invention relates to topical compositions and methods for treating dry skin, particularly in patients who are susceptible to acne-like skin lesions when the production of sebum in the skin is increased.

BACKGROUND OF THE INVENTION

In my prior co-pending application, a method was described for using dehydroepiandrosterone (DHEA) as a topical product to increase the production of sebum and thereby retard or reduce skin dryness. That method involved administering topically to the area of dry skin of the patient an effective amount of DHEA and/or a pharmaceutically acceptable, therapeutically effective derivative thereof. The DHEA could be administered in a non-toxic dermatologically acceptable vehicle, such as a tincture, cream, ointment, or gel.

It has been found, however, that there are concentrations at which DHEA is used in treating dry skin such that the increase in sebum has been accompanied by or associated with the formation of acne-like skin lesions in people who have the genetic tendency for acne. Conventional over-the-counter preparations for treating acne generally act as drying agents and exfoliators, which are generally irritating to the skin and counter-productive to the general treatment of dry skin. According, it would be advantageous to have a composition which could counteract the formation of acne-like skin lesions without diminishing the effectiveness of DHEA in improving the sebaceous gland activity of the skin.

It has been reported that alpha-hydroxycarboxyclic acids such as glycolic, tartaric, lactic and mandelic acid have been reported in the literture to be effect keratolytic agents. See e.g., E. J. Van Scott and R. J. Yu, "Substances that Modify the Stratum Corneum by Modulating its Formation", Chapter 10 of *Principles of Cosmetics for the Dermatologist,* edited by Philip Frost and Stephen N. Horwitz. Moreover, salicylic acid (orthohydroxybenzoic acid) is a known keratolyic agent present in an amount of about 2 percent by weight in over-the-counter preparations such as "PERMOX", "FOSTEX" and "FOSTRIL", used in the treatment of acne. However, these known exfoliators have not to applicant's knowledge been used in preparations to prevent acne formation.

BRIEF SUMMARY OF THE INVENTION

There have now been discovered DHEA formulations and methods for treating dry skin, particularly for patients who have a genetic tendency for acne. The topical compositions of the invention comprise DHEA and/or a pharmaceutically acceptable, therapeutically effective derivative or analog thereof, a keratolytic agent and a non-toxic dermatologically acceptable vehicle. The DHEA and/or derivative thereof is present in an amount which is effective to increase sebum production, while the keratolytic agent is present in an amount sufficient to counteract the formation of acne-like skin lesions without diminishing the effectiveness of dehydroepiandrosterone or its derivative.

The preferred keratolytic agents are selected from hydroxybenzoic acids, alpha-hydroxycarboxylic acids and urea. Ortho-hydroxybenzoic acid (salicylic acid) is particularly preferred. The vehicle may be any of a wide variety of preferably non-drying preparations such as tinctures, creams, ointments, gels and lotions.

DETAILED DESCRIPTION OF THE INVENTION

As disclosed in my co-pending application Ser. No. 408,548, the sebum excretion rate in animal skin, particularly human skin, may be increased by the topical application DHEA, either in the form of the free alcohol or in the form of one or more of the analogs or derivatives of DHEA, e.g., the acetate, valerate, enanthate, and fatty acid ester derivatives. As used hereafter in this application unless indicated otherwise, any reference to DHEA will be understood to refer to DHEA and/or derivatives or analogs thereof. The free alcohol form of DHEA is preferred and was used in the specific examples below.

Typical formulations in my prior application Ser. No. 408,548 contained about 1 weight percent DHEA based on the total weight of the formulation, as that amount was found to be effective when topically applied to the area of dry skin to increase the sebum production rate and thereby reduce or retard dryness of the skin. Such topical applications were found to be essentially local in effect with substantially no systemic effect or undesirable side effects.

According to the present invention, effective formulations may contain about 0.01 to 1.0 weight percent DHEA, typically about 1 weight percent. It has been found that DHEA concentrations on the order of about 0.1 weight percent of the formulation of the present invention are as effective as my prior DHEA formulations is sebum production while preventing the side effect of acne-like skin lesions in certain patients. Concentrations above about 1.0 weight percent DHEA could be used but produce no significant increased effect and are therefore wasteful.

According to the invention of my prior co-pending application, DHEA was found to be so potent in increasing sebum production that acne was being caused in patients who have the genetic tendency to such conditions. That is, the increased sebum was found to form the hardened plugs which clog the pores and cause the formation of cysts which are characteristic of acne and acne-like conditions. The incorporation of a keratolytic agent in the compositions of the present invention was found to substantially prevent the occurence of such conditions.

The keratolytic agents used in the formulations and methods of the present invention may include hydroxybenzoic acids, including ortho, meta or para hydroxybenzoic acids; alpha-hydroxycarboxylic acids, such as glycolic, tartaric, lactic or mandelic acids; or urea. Particularly preferred according to the invention is orthohydroxybenzoic acid (salicylic acid), which is a known exfoliator in topical over-the-counter acne treatment preparations, as well as being used in topical preparations for the treatment of warts, corns, calluses, seborrheic disorders, etc.

When salicylic acid is used as the keratolytic agent in the formulations of the invention, it is preferably present in the amount of about 0.1 to 2 percent by weight. Other keratolytic agents, which are not as strong as salicyclic acid, may be used in the formulations of the invention in concentrations of about 0.1 to 10 percent by weight of the formulation. The exact concentration of keratolytic agent to be used in the invention will vary somewhat depending upon the particular form of dosage chosen, e.g., ointment, cream, lotion, etc., but may be determined by one of ordinary skill in the art with a minimum of experimentation.

As demonstrated in the specific examples below the compositions of the present invention may contain conventional vehicle ingredients to form lotions, tinctures, creams, gels or ointments which are non-toxic and dermatologically acceptable. In addition to these and other vehicles which will be obvious to those of ordinary skill in the art, it will be understood that the compositions of the present invention may include other ingredients such as hydrocortisone moisturizers, benzoyl peroxide, antibiotics, etc.

The following specific, non-limiting examples concern the preparation of a topical lotion, topical cream, topical ointment and topical gel, respectively, using vehicles previously used in other preparations and reformulated to optimize the efficacy of the DHEA and keratolytic agent. The formulations for these preparations are given in Table I hereinbelow.

EXAMPLE NO. 1

Propylene glycol and water were mixed and dissolved into alcohol. The resultant vehicle mixture, salicylic acid and DHEA were mixed and dissolved. The resultant formulation was a topical lotion or tincture.

EXAMPLE NO. 2

In this example a topical cream was prepared by first mixing the melting propylparaben, stearic acid, cetyl alcohol, glyceryl monostearate, lanolin oil, mineral oil and sesame oil at 70 degrees C. A second mixture was formed by mixing and dissolving methylparaben, triethanolamine and propylene glycol in water at 70 degrees C. The second mixture was slowly added to and mixed with the first mixture to form an emulsion. DHEA, salicylic acid and Carbomer 940 were dispersed in the resultant emulsion at 50 degrees C. The resultant composition was slowly cooled with mixing until the composition reached room temperature.

EXAMPLE NO. 3

In this example a topical ointment was prepared. As a first step, glyceryl monostearate was mixed and melted in petrolatum at 70 degrees C. As a second step, DHEA and salicylic acid were mixed and dissolved in propylene glycol at 70 degrees C. The resultant composition of step 2 was slowly added to the resultant composition of step 1, with mixing. This mixture was then cooled to room temperature without mixing.

EXAMPLE NO. 4

In this example a topical gel was prepared. As a first step, hydroxy propyl cellulose was hydrated and dissolved into water. As a second step, DHEA, salicylc acid, butylene glycol and PPG-12-Buteth-16 were dissolved in alcohol. Slowly the resultant mixture of step 2 was added into the resultant mixture of step 1 with mixing until a gel formed.

TABLE I

| | DHEA - Salicylic Acid Formulations | | | |
|---|---|---|---|---|
| Ingredients | Example No. 1 Topical Lotion % w/w | Example No. 2 Topical Cream % w/w | Example No. 3 Topical Oint. % w/w | Example No. 4 Topical Gel % w/w |
| Actives | | | | |
| DHEA (free alcohol) | 1.0 | 1.0 | 1.0 | 1.0 |
| Salicylic acid | 1.0 | 1.0 | 1.0 | 1.0 |
| Inactives | | | | |
| Methylparaben | | 0.1 | | |
| Propylparaben | | 0.1 | 0.1 | |
| Hydroxy propyl cellulose (1) | | | | 1.0 |
| PPG-12-Buteth-16 (2) | | | | 2.0 |
| Lanolin oil | | 5.0 | | |
| Mineral oil | | 4.0 | | |
| Sesame oil | | 4.0 | | |
| Cetyl alcohol | | 5.0 | | |
| Glyceryl monostearate | | 2.0 | 3.0 | |
| Stearic acid | | 2.0 | | |
| Triethanolamine | | 1.0 | | 0.2 |
| Propylene glycol | 5.0 | 5.0 | 12.0 | 5.0 |
| Alcohol (3) | 87.0 | | | 45.0 |
| Carbomer 940 (4) | | 0.1 | | 0.2 |
| Petrolatum | | | 82.9 | |
| Water | 6.0 | 69.7 | | 42.4 |
| | 100.0 | 100.0 | 100.0 | 100.0 |

Notes:
(1) available under the trademark Klucel$^R$ from Hercules
(2) available under the trademark Ucon$^R$ fluid 50 HB from Union Carbide
(3) contains 95% ethanol and 5% water
(4) available under the trademark Carbopol 940$^R$ from B.F. Goodrich It will be recognized by those skilled in the art that changes may be made to the above-described embodiments of the invention without departing from the broad inventive concepts thereof. It is understood, therefore, that this invention is not limited to the particular embodiments disclosed, but it is intended to cover all modifications which are within the scope and spirit of the invention as defined by the appended claims.

I claim:

1. A topical composition for treating dry skin in a patient comprising:
   a. dehydroepiandrosterone and/or a pharmaceutically acceptable, therapeutically effective derivative thereof in an amount effective to increase sebum production;
   b. a keratolytic agent in an amount sufficient to counteract the formation of acne-like skin lesions without diminishing the effectiveness of dehydroepiandrosterone or its derivative; and
   c. a non-toxic, dermatologically acceptable vehicle.

2. A composition according to claim 1 wherein said keratolytic agent is selected from the group consisting of hydroxybenzoic acids, alpha-hydroxycarboxylic acids and urea.

3. A composition according to claim 2 wherein said alpha-hydroxycarboxylic acid is selected from the group consisting of glycolic, tartaric, lactic and mandelic acids.

4. A composition according to claim 3 wherein said keratolytic agent is present in an amount of about 0.1 to 10 weight percent of the composition.

5. A composition according to claim 2 wherein said keratolytic agent is salicylic acid.

6. A composition according to claim 5 wherein said salicylic acid is present in an amount of about 0.1 to 2 weight percent of the composition.

7. A composition according to claim 1 wherein said dehydroepiandrosterone and/or derivative thereof is present in an amount of about 0.01 to 1.0 weight percent of the composition.

8. A composition according to claim 1 wherein dehydroepiandrosterone free alcohol is present in an amount of about 1.0 weight percent and said keratolytic agent is salicylic acid present in an amount of about 1.0 weight percent of the composition.

9. A composition according to claim 1 wherein said vehicle is selected from the group consisting of tinctures, creams, ointments, gels and lotions.

10. A method of treating dry skin in a patient which comprises topically administering to the area of dry skin in the patient a composition comprising (a) an effective amount of dehydroepiandrosterone and/or a pharmaceutically acceptable, therapeutically effective derivative thereof and (b) a keratolytic agent in an amount sufficient to counteract the formation of acne-like skin lesions without diminishing the effectiveness of dehydroepiandrosterone or its derivative.

11. A method according to claim 10 wherein said keratolytic agent is salicylic acid.

12. A method according to claim 10 wherein said salicylic acid comprises about 0.1 to 2 weight percent of said composition.

13. A method according to claim 10 wherein said keratolytic agent is an alpha-hydroxycarboxylic acid in an amount of about 0.1 to 10 weight percent of the composition.

14. A method according to claim 10 wherein said patient has a genetic tendency for acne.

15. A method according to claim 10 wherein said composition contains about 0.01 to 1 weight percent dehydroepiandrosterone and/or derivative thereof.

16. A method according to claim 10 wherein said composition is administered in a non-toxic, dermatologically acceptable vehicle selected from the group consisting of tinctures, creams, ointments, gels and lotions.

* * * * *